US00PP37078P2

(12) United States Plant Patent
Guerrero

(10) Patent No.: US PP37,078 P2
(45) Date of Patent: Nov. 4, 2025

(54) ***ROSA* PLANT NAMED 'ESM R896'**

(50) Latin Name: *Rosa hybrida*
Varietal Denomination: ESM R896

(71) Applicant: GENVIV HOLDINGS, LLC, Miami, FL (US)

(72) Inventor: Maria Elena Guerrero, Quito (EC)

(73) Assignee: GENVIV HOLDINGS, LLC, Miami, FL (US)

( * ) Notice: Subject to any disclaimer, the term of this patent is extended or adjusted under 35 U.S.C. 154(b) by 0 days.

(21) Appl. No.: 19/210,855

(22) Filed: May 16, 2025

(51) Int. Cl.
*A01H 5/02* (2018.01)
*A01H 6/74* (2018.01)

(52) U.S. Cl.
USPC ..... Plt./105
CPC ..... *A01H 6/749* (2018.05)

(58) Field of Classification Search
USPC ..... Plt./105
CPC ..... A01H 5/0222
See application file for complete search history.

*Primary Examiner* — Kent L Bell
(74) *Attorney, Agent, or Firm* — C. Anne Whealy

(57) ABSTRACT

A new and distinct cultivar of Rose plant named 'ESM R896', characterized by its upright and relatively strong flowering stems; relatively moderately vigorous growth habit; dark green-colored leaves; orange-colored flower petals and petaloids that become darker orange with development giving the flower a bi-colored appearance; petals and petaloids are relatively resistant to bruising; and excellent postproduction longevity.

1 Drawing Sheet

Botanical designation: *Rosa hybrida.*
Cultivar denomination: 'ESM R896'.

CROSS-REFERENCED TO CLOSELY-RELATED APPLICATIONS

An European Community Plant Breeder's Rights application for the instant plant was filed by the Applicant/Assignee of the instant application, Genviv Holdings, LLC of Miami, Florida on Apr. 18, 2025, application No. 2025/0850. Foreign priority is not claimed to this European Community Plant Breeder's Rights application.

BACKGROUND OF THE INVENTION

The present Invention relates to a new and distinct cultivar of Rose plant, botanically known as *Rosa hybrida*, commercially used as a cut flower Rose plant, and hereinafter referred to by the name 'ESM R896'.

The new Rose plant is a product of a planned breeding program conducted by the Inventor in El Quinche, Pichincha, Ecuador. The objective of the breeding program was to develop new cut flower Rose varieties with unique flower colors and excellent postproduction longevity.

The new Rose plant originated from a cross-pollination made by the Inventor in March 2020 of a proprietary Rose selection identified as line 974, not patented, as the female, or seed, parent with a proprietary Rose selection identified as line 1019, not patented, as the male, or pollen, parent. The new Rose plant was discovered and selected by the Inventor as a single flowering plant within the progeny of the stated cross-pollination in a controlled greenhouse environment in El Quinche, Pichincha, Ecuador in August 2021.

Asexual reproduction of the new Rose plant by bud grafting in El Quinche, Pichincha, Ecuador since January 2022 has shown that the unique features of this new Rose plant are stable and reproduced true to type in successive generations of asexual reproduction.

SUMMARY OF THE INVENTION

Plants of the new Rose have not been observed under all possible combinations of environmental conditions and cultural practices. The phenotype may vary somewhat with variations in environmental conditions such as temperature and light intensity, without however, any variance in genotype.

The following traits have been repeatedly observed and are determined to be the unique characteristics of 'ESM R896'. These characteristics in combination distinguish 'ESM R896' as a new and distinct Rose plant:

1. Upright and relatively strong flowering stems.
2. Relatively moderately vigorous growth habit.
3. Dark green-colored leaves.
4. Orange-colored flower petals and petaloids that become darker orange with development giving the flower a bi-colored appearance.
5. Petals and petaloids are relatively resistant to bruising.
6. Excellent postproduction longevity.

Plants of the new Rose differ from plants of the female parent selection in the following characteristics:

1. Plants of the new Rose are not as productive as plants of the female parent selection.
2. Flower buds of plants of the new Rose are shorter than flower buds of plants of the female parent selection.
3. Flowers of plants of the new Rose have fewer petals than flowers of plants of the female parent selection.

Plants of the new Rose differ from plants of the male parent selection in the following characteristics:

1. Flower buds of plants of the new Rose are shorter than flower buds of plants of the male parent selection.

2. Flowers of plants of the new Rose have fewer petals than flowers of plants of the male parent selection.
3. Flowers of plants of the new Rose are orange in color whereas flowers of plants of the male parent selection are brown in color.

Plants of the new Rose can also be compared to plants of *Rosa hybrida* 'Silantoi', not patented. In side-by-side comparisons, plants of the new Rose differ from plants of 'Silantoi' in the following characteristics:

1. Developed stems of plants of the new Rose are darker brownish green in color than developed stems of plants of 'Silantoi'.
2. Plants of the new Rose have smaller flowers than plants of 'Silantoi'.
3. Flowers of plants of the new Rose are darker orange in color than flowers of plants of 'Silantoi'.

BRIEF DESCRIPTION OF THE PHOTOGRAPH

The accompanying colored photographic sheet illustrates the overall appearance of the new Rose plant showing the colors as true as it is reasonably possible to obtain in colored reproductions of this type. Colors in the photograph may differ slightly from the color values cited in the detailed botanical description which accurately describe the colors of the new Rose plant.

On the left side of the photographic sheet is a side perspective view of a typical flowering stem of 'ESM R896'.

At the upper right of the photographic sheet is a close-up view of a typical developed flower of 'ESM R896'.

And at the lower right of the photographic sheet are close-up views of the upper and lower surfaces of typical leaves of 'ESM R896'.

DETAILED BOTANICAL DESCRIPTION

The aforementioned photographic sheet and the following observations and measurements describe plants grown in ground beds in a polyethylene-covered greenhouse in Cayambe, Pichincha, Ecuador and under typical cut Rose production practices. Plants were grown year round and were 17 months old when the photographs and the description were taken. During the production of the plants, day temperatures ranged from 17° C. to 21° C., night temperatures ranged from 5° C. to 8° C. and light levels averaged 19,338 lux. In the following description, color references are made to The Royal Horticultural Society Colour Chart, 2015 Edition, except where general terms of ordinary dictionary significance are used.

Botanical classification: *Rosa hybrida* 'ESM R896'.

Parentage:

*Female, or seed, parent*.—Proprietary seedling selection of *Rosa hybrida* identified line 974, not patented.

*Male, or pollen, parent*.—Proprietary seedling selection of *Rosa hybrida* identified line 1019, not patented.

Propagation:

*Type*.—By bud grafting.

*Time to initiate roots, summer*.—About seven to ten days at temperatures about 26° C. to 30° C.

*Time to produce a rooted young plant, summer*.—About four to five weeks at temperatures about 22° C. to 26° C.

*Root description*.—Medium in thickness, fibrous; typically close to 200A in color, actual color of the roots is dependent on substrate composition, water quality, fertilizers, substrate temperature and age of roots.

*Rooting habit*.—Freely branching; medium density.

Plant description:

*Plant and growth habit*.—Perennial shrub; upright and strong flowering stems; typically grown as a standard type; relatively moderate vigorous growth habit and moderate growth rate.

*Productivity*.—Plants of the new Rose are highly productive with about eleven flowering stems developing per plant per year.

*Plant height*.—About 105 cm.

*Plant width* (*spread*).—About 41 cm.

*Lateral branches*.—Length: About 75.6 cm. Diameter: About 5.1 mm. Internode length: About 5.8 cm. Texture and luster: Smooth, glabrous; semi-glossy. Strength: Relatively strong. Color, developing: Close to 183A. Color, developed: Close to N200A tinged with close to NN137A; at the internodes, close to 144A tinged with close to 185A. Thorns: Density: About one to two thorns per linear cm. Height: About 1 cm. Length, at base: About 5.5 mm. Color, immature: Close to 181A. Color, mature: Close to 176A.

Leaf description:

*Arrangement*.—Alternate; compound with typically five leaflets per leaf.

*Leaf length*.—About 15 cm.

*Leaf width*.—About 9.2 cm.

*Leaflet length*.—About 5.4 cm.

*Leaflet width*.—About 4.5 cm.

*Leaflet shape*.—Ovate with cordate tendencies.

*Leaflet apex*.—Acuminate.

*Leaflet base*.—Obtuse with cordate tendencies.

*Leaflet margin*.—Serrate.

*Leaflet texture and luster, upper surface*.—Smooth, glabrous; semi-glossy.

*Leaflet texture and luster, lower surface*.—Smooth, glabrous; matte.

*Leaflet venation pattern*.—Pinnate and arcuate.

*Leaflet color*.—Developing leaflets, upper surface: Close to 141A tinged with close to N77A. Developing leaflets, lower surface: Close to NN137A tinged with close to 178A. Fully expanded leaflets, upper surface: Close to NN137A; venation, close to 152A. Fully expanded leaflets, lower surface: Close to 146B; venation, close to 144C and 146D.

*Petioles*.—Length: About 3.4 cm. Diameter: About 2 mm. Strength: Relatively moderately strong. Texture and luster, upper surface: Slightly hirsutulous; semi-glossy. Texture and luster, lower surface: Smooth, glabrous; semi-glossy. Color, upper surface: Close to NN137A. Color, lower surface: Close to 147B.

*Stipules*.—Arrangement and appearance: Two, adnate to the petiole, leafy in appearance. Length: About 2.6 cm. Width: About 3.3 mm. Shape: Roughly deltoid. Apex: Acute. Base: Tapered. Margin: Ciliate. Texture and luster, upper and lower surfaces: Smooth, glabrous; membranous; matte. Venation pattern: Pinnate. Color, upper surface: Close to NN137A. Color, lower surface: Close to 146B.

Flower description:

*Flower type and arrangement*.—Symmetrical rosette flowers; flowers typically grown as standard types with one terminal flower per flowering stem; flowers face upright.

*Flowering season*.—Plants of the new Rose flower year-round under greenhouse conditions in Ecuador; plants begin flowering about 85 to 90 days after planting young plants.

*Flower diameter*.—About 10.6 cm.

*Flower depth* (*height*).—About 5.7 cm.

*Flower longevity*.—Excellent postproduction longevity; flowers maintain good substance for about six weeks on the plant and for about 12 to 14 days as a cut flower; flowers persistent; flowers are relatively resistant to bruising during transport.

*Fragrance*.—None detected.

*Flower buds*.—Length: About 4.6 cm. Diameter: About 3.2 cm. Shape: Ovoid. Texture and luster: Smooth, glabrous; matte. Color: Close to 47A.

*Petals*.—Quantity: About 36 to 38 per flower in about six whorls; petals imbricate. Length: About 5.7 cm. Width: About 5.5 cm. Shape: Obovate to rounded. Apex: Rounded. Base: Rounded. Margin: Entire, recurved; slightly undulate. Texture and luster, upper and lower surfaces: Smooth, glabrous; matte. Color: When opening, upper surface: Close to 47A. When opening, lower surface: Close to 42A. Fully opened, upper surface: Close to 31C and becoming closer to 34C; venation, close to 15A; color becoming closer to 35C with subsequent development. Fully opened, lower surface: Close to 168B; venation, close to 14A and 14C; color becoming closer to 179B with subsequent development.

*Petaloids*.—Quantity: About five to seven in a single whorl; size and shape are variable. Length: About 2.1 cm. Width: About 1.6 cm. Texture and luster, upper surface: Somewhat rugose, glabrous; matte. Texture and luster, lower surface: Smooth, glabrous; matte. Color: When opening, upper surface: Close to 39B. When opening, lower surface: Close to 35C. Fully opened, upper surface: Close to 169C; venation, close to 14C; color becoming closer to 168B and 179B with subsequent development. Fully opened, lower surface: Close to 34B; venation, close to 14A and 14B; color becoming closer to 171C and 180C with subsequent development.

*Sepals*.—Quantity per flower: Typically five in a single whorl. Length: About 5.3 cm. Width: About 1.1 cm. Shape: Lanceolate. Apex: Acuminate. Base: Truncate. Margin: Entire; slightly ciliate to ciliolate. Texture and luster, upper surface: Slightly pubescent; matte. Texture and luster, lower surface: Moderately pubescent; matte. Color: When opening, upper surface: Close to 144A. When opening, lower surface: Close to 144B. Fully opened, upper surface: Close to 146B. Fully opened, lower surface: Close to 144A.

*Reproductive organs*.—Stamens: Quantity: About 150 to 190 per flower. Filament length: About 7.8 mm. Filament color: Close to 14A. Anther size: About 0.3 mm by 4.4 mm. Anther shape: Reniform. Anther color: Close to 16C. Pollen amount: Scarce to moderate. Pollen color: Close to 22A. Pistils: Quantity: About 160 to 202 per flower. Pistil length: About 1.8 cm. Stigma diameter: About 1.5 mm. Stigma shape: Lobed. Stigma color: Close to 14C to 15C. Style length: About 1 cm. Style color: Close to 1C. Ovary color: Close to 1D and 4D. Receptacle height: About 7.6 mm. Receptacle diameter: About 1.3 cm. Receptacle shape: Cup-shaped. Receptacle texture: Smooth, glabrous. Receptacle color: Close to 144B. Fruits and seeds: To date, fruit and seed development have not been observed on plants of the new Rose.

Pathogen & pest tolerance: To date, plants of the new Rose have not been observed to be tolerant to pathogens and pests common to Rose plants.

Temperature tolerance: Plants of the new Rose have been observed to tolerate temperatures ranging from 9° C. to 23° C.

It is claimed:

1. A new and distinct Rose plant named 'ESM R896' as herein illustrated and described.

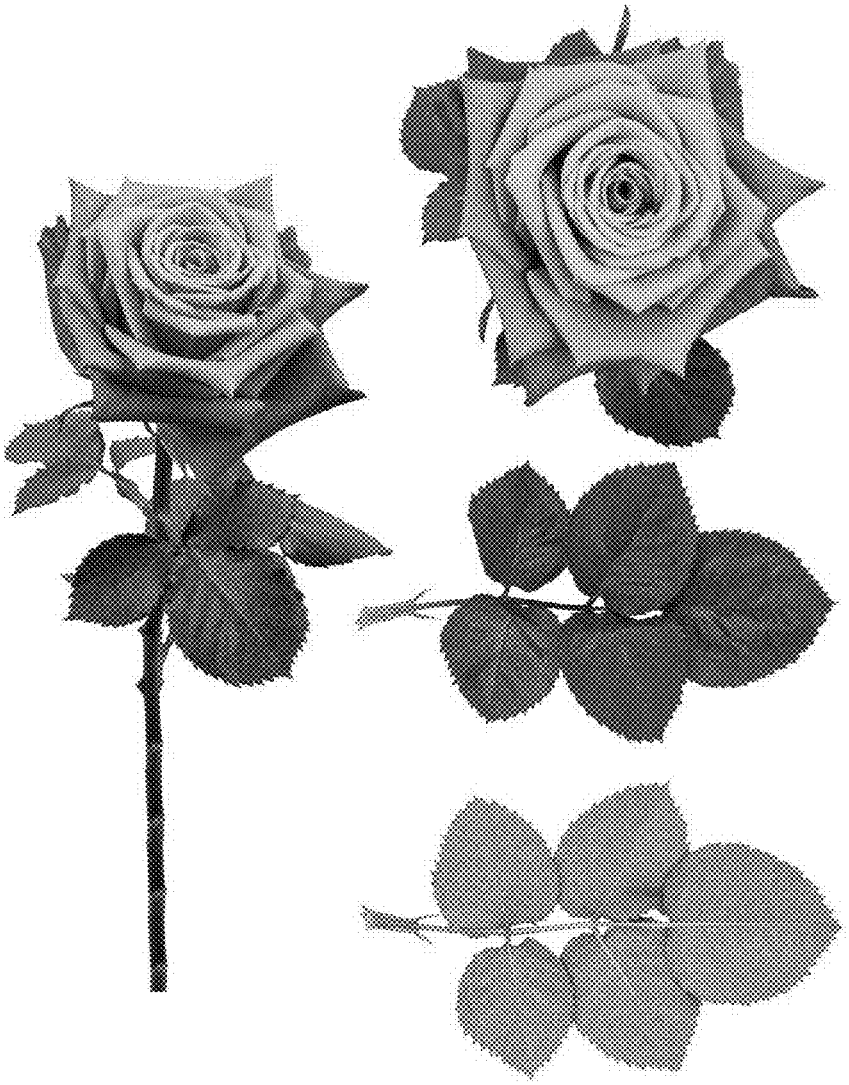

* * * * *